United States Patent
George et al.

(10) Patent No.: US 8,445,673 B2
(45) Date of Patent: May 21, 2013

(54) PROCESS FOR THE PREPARATION OF STERILE DORIPENEM

(75) Inventors: Vinod George, Malappuram (IN); Hashim Nizar Poovanathil Nagoor Meeran, Pathanamthitta (IN); Neera Tiwari, Gurgaon (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 235 days.

(21) Appl. No.: 12/934,348

(22) PCT Filed: Mar. 23, 2009

(86) PCT No.: PCT/IB2009/051211
§ 371 (c)(1),
(2), (4) Date: Dec. 3, 2010

(87) PCT Pub. No.: WO2009/118680
PCT Pub. Date: Oct. 1, 2009

(65) Prior Publication Data
US 2011/0082293 A1 Apr. 7, 2011

(30) Foreign Application Priority Data
Mar. 24, 2008 (IN) .............................. 739/DEL/2008

(51) Int. Cl.
*C07D 477/20* (2006.01)
(52) U.S. Cl.
USPC ........................................................ 540/350

(58) Field of Classification Search
USPC ........................................................ 540/350
See application file for complete search history.

(56) References Cited

U.S. PATENT DOCUMENTS

| | | | |
|---|---|---|---|
| 5,317,016 A | 5/1994 | Nishitani et al. | 514/210 |
| 5,703,243 A | 12/1997 | Nishitani et al. | 548/541 |
| 6,111,098 A | 8/2000 | Inoue et al. | 540/350 |
| 8,093,284 B2 * | 1/2012 | Nakanishi | 514/413 |
| 8,148,420 B2 * | 4/2012 | Kuo et al. | 514/425 |
| 2003/0153191 A1 | 8/2003 | Saitoh et al. | 438/694 |

FOREIGN PATENT DOCUMENTS

| WO | WO 2006/117763 | 11/2006 |
|---|---|---|
| WO | WO 2007/031858 | 3/2007 |

OTHER PUBLICATIONS

Iso et al., "A Novel 1β-Methylcarbapenem Antibiotic, S-4661: Synthesis and Structure-activity Relationships of 2-(5-Substituted Pyrrolidin-3-ylthio)-1β-methylcarbapenems", *The Journal of Antibiotics*, 49(2):199-209 (1996).

Iso et al., "Synthesis and Modification of a Novel 1β-Methyl Carbapenem Antibiotic, S-4661", *The Journal of Antibiotics*, 49(5):478-484 (1996).

Nishino et al., "Practical Large-Scale Synthesis of Doripenem: A Novel 1β-Methylcarbapenem Antibiotic", *Organic Process Research and Development*, 7(6):846-850 (2003).

* cited by examiner

*Primary Examiner* — Mark Berch

(57) ABSTRACT

The present invention relates to a process for the preparation of sterile doripenem.

8 Claims, No Drawings

PROCESS FOR THE PREPARATION OF STERILE DORIPENEM

FIELD OF THE INVENTION

The present invention relates to a process for the preparation of sterile Doripenem.

BACKGROUND OF THE INVENTION (4R,5S,6S)-3-[[(3S,5S)-5-[[(Aminosulfonyl)amino]methyl]-3-pyrrolidinyl]thio]-6-[(1R)-1-hydroxyethyl]-4-methyl-7-oxo-1-azabicyclo[3.2.0]hept-2-ene-2-carboxylic acid, commonly known as doripenem of Formula I is a synthetic broad-spectrum carbapenem antibiotic.

FORMULA I

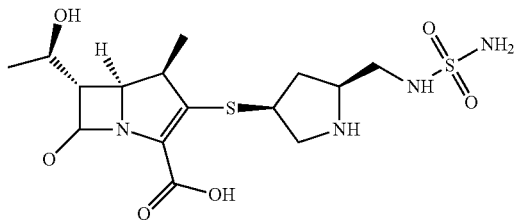

Doripenem is available in the market as a monohydrate and it exhibits potent, broad and well-balanced antibacterial activity against a wide range of both Gram-positive and Gram-negative bacteria including *Pseudomonas aeruginosa*.

U.S. Pat. No. 5,317,016 provides a process for the isolation of doripenem from the reaction mixture by layer separation followed by lyophilization of the aqueous layer. Doripenem is obtained in the above process with a purity of 85%. Similar processes for preparing lyophilized doripenem have also been described in Yasuyoshi Iso, et al., J. Antibiot., 49, pages 199-209 (1996), and Yasuyoshi Iso, et al., J. Antibiot., 49, pages 478-484 (1996). PCT Publication No. WO 2006/117763 provides a process for the isolation of amorphous doripenem from the reaction mixture by layer separation followed by the addition of the aqueous layer to methanol. PCT Publication No. WO 2006/117763 also provides a process for preparing amorphous doripenem by pouring an aqueous solution of doripenem into ethanol. U.S. Pat. Nos. 6,111,098 and 5,703,243 provide processes for preparing crystalline and amorphous lyophilization products of doripenem by lyophilizing the aqueous solutions of doripenem. U.S. Patent Application No. 2003/0153191 provides processes for preparing Type III crystals of doripenem from an aqueous solution of doripenem using Type III seed crystals. According to U.S. Patent Application No. 2003/0153191, the starting aqueous solution is prepared by heating a mixture of water and crude doripenem to 50° to 55° C. and filtering it through activated carbon at a temperature of at least 50° C.

Yutaka Nishino, et al., Org. Process Res. Dev., 7, pages 846-850 (2003), provides a process for the preparation of sterile crystalline doripenem, wherein, crude doripenem is dissolved in water by heating at 55° C., filtered through a funnel pre-coated with activated carbon, a membrane filter (0.2 mm), a membrane for ultra filtration and a filter for the sterilization. The solution is cooled to room temperature, and stirred at 2° C. for 2 hours. Isopropanol is then added and stirred at −5° C. for 4 hours and at −10° C. overnight to obtain sterile doripenem.

SUMMARY OF THE INVENTION

The prior art processes for preparing sterile doripenem require dissolving doripenem in water to obtain aqueous solution. According to the prior art processes, the aqueous solution of doripenem is prepared by heating to a temperature above 50° C. for dissolution and the processes also require filtration under hot conditions. The present inventors have observed that carrying out dissolution and/or sterilization or filtration of doripenem, which is a heat sensitive compound, at high temperature conditions result in the formation of degradation impurities. The present inventors have developed an advantageous process for the preparation of sterile doripenem, which can be carried out at low temperature conditions and thereby minimizing the degradation. By employing the process of the present invention, doripenem can also be obtained as a monohydrate. Further, the present process is simple and efficient to prepare sterile doripenem at industrial scale.

DETAILED DESCRIPTION OF THE INVENTION

A first aspect of the present invention provides a process for preparation of sterile doripenem, wherein the process comprises:
 a) dissolving doripenem in water in the presence of a base,
 b) filtering the solution obtained in step a) using a filter for sterilization, and
 c) isolating sterile doripenem from the filtered solution thereof.

Doripenem, which is used as the starting material, may be prepared according to the methods provided in U.S. Pat. Nos. 5,317,016 and. 6,111,098 or Yutaka Nishino, et al., Org. Process Res. Dev., 7, pages 846-850 (2003). Doripenem, which is used as the starting material, can exist in any solid form known in the art. Doripenem is dissolved in water in the presence of a base. The base may be selected from the group consisting of hydroxides, bicarbonates or carbonates of alkali metals or alkaline earth metals, alkoxides and amines. The water may be used in a quantity of about 5 times to about 15 times to the weight of doripenem. The base may be used in an amount required to attain a pH of about 8 to about 12 at a temperature of about 30° C. or below, for example, at a temperature of about 5° C. to about 25° C. The solution so obtained is optionally treated with activated carbon and filtered using a filter for sterilization. The filter for sterilization is, for example, a membrane having a pore diameter of about 0.25 microns or below. Sterile doripenem is isolated from the filtered solution. The isolation may be carried out by adjusting the pH of the filtered solution to about 4 to about 6. The pH adjustment may be carried out by the addition of an acid. The acid may be an organic or inorganic acid. The acid may be used in concentrated form or as diluted solutions. The mixture so obtained is optionally seeded with sterile doripenem and stirred at about 0° to about 30° C. The stirring may be carried out for about 10 minutes to about 100 hours, for example, for about 1 to about 6 hours. Sterile doripenem may be isolated from the mixture as a monohydrate by filtration, concentration, distillation, treating with water miscible organic solvent or a combination thereof. Sterile doripenem monohydrate is, for example, isolated by treating the mixture with a water miscible organic solvent. The water miscible organic solvent may be selected from the group consisting of acetone, acetonitrile, tetrahydrofuran, dimethylsulfoxide, methanol, ethanol, propanol, dimethylformamide and dioxane. The mixture may be stirred and filtered to obtain sterile doripenem monohydrate.

While the present invention has been described in terms of its specific embodiments, certain modifications and equivalents will be apparent to those skilled in the art and are intended to be included within the scope of the present invention.

EXAMPLE

Preparation of Sterile Doripenem Monohydrate

Doripenem (50 g) was dissolved in water (300 ml) by adding ammonia drop-wise to attain a pH of 8.5 to 9 at 15° to 20° C. The solution was treated with activated carbon (5 g) followed by micron filtration using a membrane (0.25 microns). The pH of the filtrate was adjusted to 5 to 5.5 with aqueous formic acid at 10° to 20° C. The mixture was stirred at 0° to 5° C. for 4 to 5 hours. Isopropyl alcohol (150 ml) was added slowly to the mixture and stirred for about 12 hours at 0° to 5° C. The mixture was filtered and dried at 40° to 50° C. to obtain the title compound.

Yield: 80% w/w
Purity: 98%

We claim:

1. A process for preparation of sterile doripenem monohydrate, wherein the process comprises,
   a) dissolving doripenem in water in the presence of a base,
   b) filtering the solution obtained in step a) using a filter for sterilization,
   c) adjusting the pH of the filtered solution between about 4 and about 6 to obtain doripenem monohydrate, and
   d) isolating sterile doripenem monohydrate obtained in step c).

2. A process according to claim 1, wherein doripenem is dissolved at a temperature of not more than about 30° C.

3. A process according to claim 1, wherein the base is selected from the group consisting of hydroxides, bicarbonates or carbonates of alkali metals or alkaline earth metals, alkoxides and amines.

4. A process according to claim 1, wherein the water is used in a quantity of about 5 times to about 15 times with respect to the weight of doripenem.

5. A process according to claim 1 or 2, wherein the base is used to maintain the pH between about 8 and about 12.

6. A process according to claim 5, wherein the base is added at a temperature range of about 5° C. to about 25° C.

7. A process according to claim 1, wherein the filter for sterilization is preferably a membrane having a pore diameter of about 0.25 microns or below.

8. A process according to claim 1, wherein the pH adjustment in step c) is carried out by the addition of formic acid.

* * * * *